(12) United States Patent
Cummings et al.

(10) Patent No.: US 6,225,071 B1
(45) Date of Patent: *May 1, 2001

(54) METHODS OF SCREENING FOR COMPOUNDS WHICH MIMIC GALECTIN-1

(75) Inventors: Richard D. Cummings, Edmond; Moon-Jae Cho, Oklahoma City, both of OK (US)

(73) Assignee: The Board of Regents of the University of Oklahoma

( * ) Notice: Subject to any disclaimer, the term of this patent is extended or adjusted under 35 U.S.C. 154(b) by 0 days.

This patent is subject to a terminal disclaimer.

(21) Appl. No.: 09/346,442

(22) Filed: Jul. 1, 1999

Related U.S. Application Data

(63) Continuation of application No. 08/929,291, filed on Sep. 5, 1997, now Pat. No. 5,948,628.

(51) Int. Cl.[7] .............................. G01N 33/53; C12N 5/08
(52) U.S. Cl. ........................ 435/7.24; 435/18; 435/375
(58) Field of Search ...................... 435/7.24, 18, 375; 514/8; 530/396

(56) References Cited

U.S. PATENT DOCUMENTS 5,587,460  12/1996  Nedwin et al. .................... 530/396

FOREIGN PATENT DOCUMENTS

| 0337799 | 10/1989 | (EP) . |
| 2249312 | 5/1992 | (WO) . |
| 9411497 | 5/1994 | (WO) . |
| 9731107 | 8/1997 | (WO) . |

OTHER PUBLICATIONS

Perillo, N.L. Galectin–1, an endogenous lectin produced by thymic epithelial cells, induces apoptosis of human thymocytes. J. Exp. Med. 185(10):1851–1858, May 1997.*

Homburg et al., "Human Neutrophils Lose their Surface FcγRII and Acquire Annexin V Binding Sites During Apoptosis In Vitro", *Blood*, vol. 85, No. 2, pp. 532–540, Jan. 15, 1995.

Perillo et al., "Apoptosis of T–Cells Mediated by Galectin–1", *Nature*, vol. 378, pp. 736–739, Dec. 14, 1995.

R.D. Cummings and M. Cho, "Characterization of Monomeric Forms of Galectin–1 Generated by Site–Directed Mutagenesis", *Biochemistry*, vol. 35, No. 40, pp. 13081–13088, Dec. 1996.

Timoshenko et al., "*Viscum album* Agglutinin–induced Aggregation of Blood Cells and the Lectin Effects on Neutrophil Function," *Biomed & Pharmacother*, 49:153–158, 1995.

Perillo et al., "Galectins: Versatile Modulators of Cell Adhesion, Cell Proliferation, and Cell Death", *J. Mol. Med.*, 76:402–412, 1998.

Cummings et al., Cummings et al., "P–Selectin and Galectin Interactions with Human Neutrophils", *Book of Abstracts, 215th ACS National Meeting*, Dallas, XP–002090743, Mar. 29, 1998.

Fouillit et al., "Affinity Purification and Characterization of Recombinant Human Galectin–1", *Journal of Chromatography*, 706(1):167–171, Feb. 27, 1998.

Cho et al., "Galectin–1, A β–Galactoside–binding Lectin in Chinese Hamster Ovary Cells," *The Journal of Biological Chemistry*, 270(10):5198–5206, 1995.

\* cited by examiner

*Primary Examiner*—David Saunders
*Assistant Examiner*—Mary Beth Tung
(74) *Attorney, Agent, or Firm*—Dunlap, Codding & Rogers, P.C.

(57) ABSTRACT

Methods for treating and modulating an inflammatory response using compositions containing a primarily monomeric or primarily dimeric form of galectin-1. The dimeric form stimulates apoptosis of activated neutrophils while the monomeric form inhibits apoptosis of activated neutrophils. Methods of screening for compounds which have galectin-1-like functions are also identified.

1 Claim, 5 Drawing Sheets

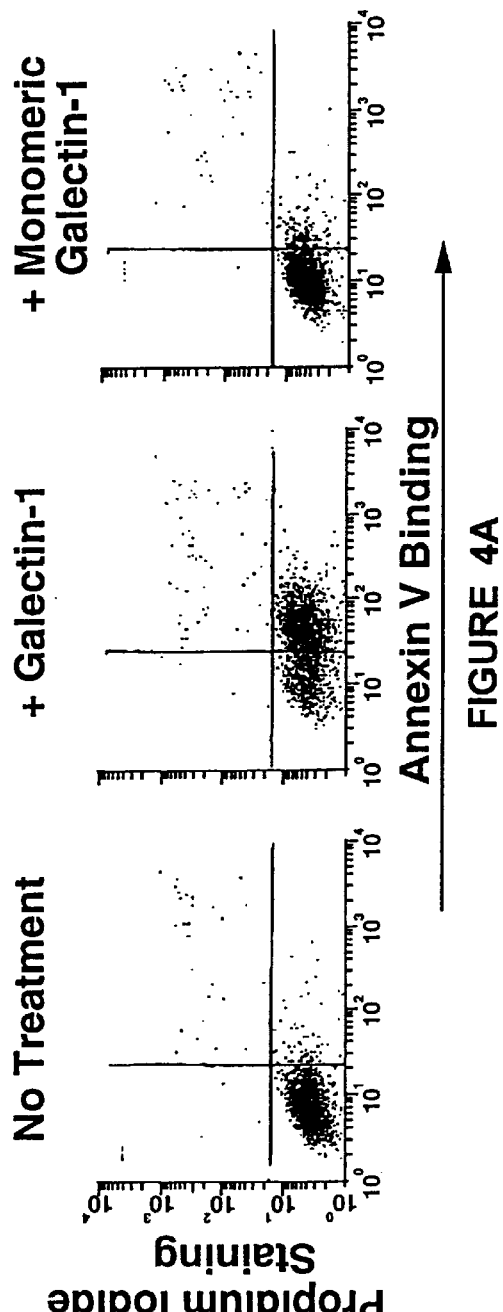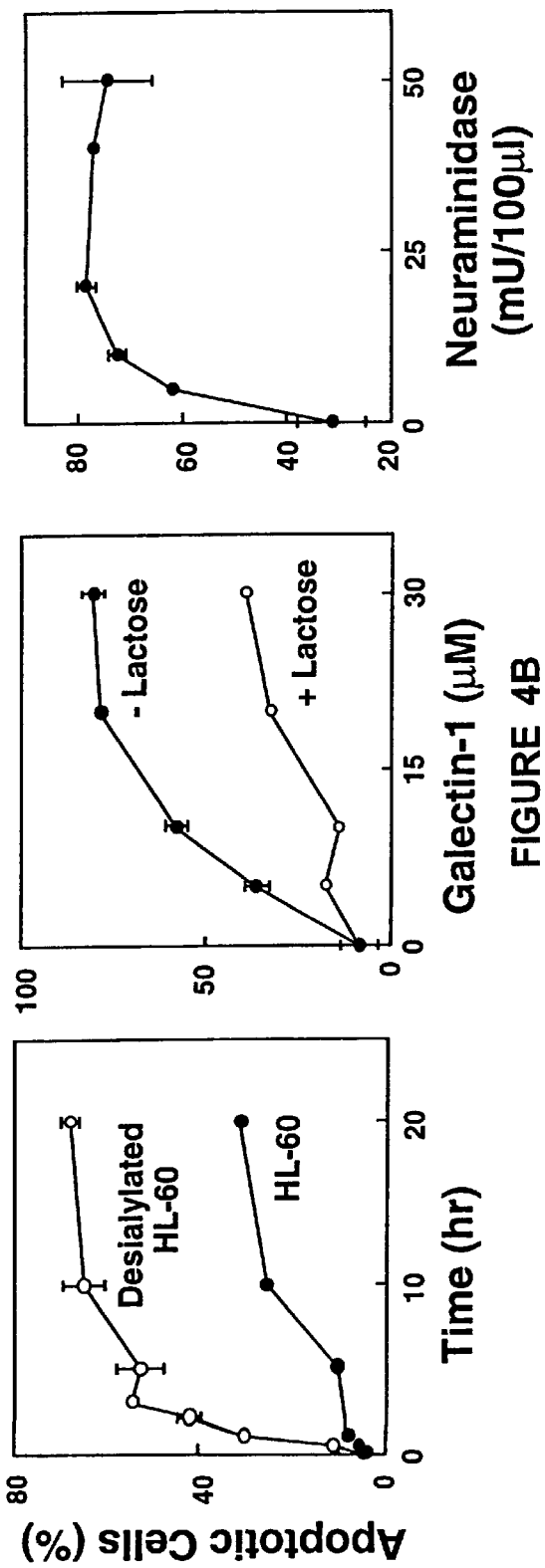
FIGURE 4A
FIGURE 4B

METHODS OF SCREENING FOR COMPOUNDS WHICH MIMIC GALECTIN-1

CROSS REFERENCE TO RELATED APPLICATIONS

This application is a continuation of U.S. Ser. No. 08/929,291, filed Sep. 5, 1997, now U.S. Pat. No. 5,948,628 entitled "METHODS OF SCREENING FOR COMPOUNDS WHICH MIMIC GALECTIN-1".

STATEMENT REGARDING FEDERALLY SPONSORED RESEARCH OR DEVELOPMENT

Not Applicable.

BACKGROUND

The present invention relates to methods of screening for compounds for use in treating and modulating an inflammatory response and, more particularly, to such methods of screening for compounds which mimic the effects of galectin-1.

Inflammation is the reaction of vascularized tissue to local injury. This injury can have a variety of causes, including infections and direct physical injury. Upon injury, the clotting system and plasmin systems are initiated together with the appropriate nervous system response to generate an initial response to facilitate immune activation. Increased blood flow, capillary permeability and chemotactic factors, including those of the complement cascade, modulate neutrophil migration to the damaged site. Neutrophils are the predominant cell type involved in acute inflammation, whereas lymphocytes and macrophages are more prevalent in chronic inflammation. The inflammatory response can be considered beneficial, since without it, infections would go unchecked, wounds would never heal, and tissues and organs could be permanently damaged and death may ensue. However, inflammation can also be potentially harmful. Inflammation causes the pathologies associated with rheumatoid arthritis, myocardial infarction, ischemic reperfusion injury, hypersensitivity reactions, and some types of fatal renal disease. The widespread problem of inflammatory diseases has fostered the development of many "anti-inflammatory" drugs. The ideal drug would be one that enhances the positive effects resulting from the inflammatory response, while preventing the potentially harmful side-effects of the inflammatory response.

The inflammatory response in regard to blood cells includes adhesion of circulating neutrophils, the most abundant phagocytic cell in the blood, to activated endothelial cells that form the lining of blood vessel walls. The adherent neutrophils are subsequently activated and emigrate from the blood into the surrounding tissue in a process termed diapedesis. The activated cells then begin engulfing microorganisms in a process termed phagocytosis. During this process the activated neutrophils release a variety of degradative enzymes, including proteolytic and oxidative enzymes into the surrounding extracellular environment. The mechanisms by which neutrophils adhere, become activated, and emigrate from the blood are currently major topics of research around the world.

Some of the important factors that mediate endothelial-neutrophil adhesion to initiate the inflammatory response are: bacterial products (e.g., endotoxin), complement fragments (e.g., C5a), chemotactic peptides, leukotriene $B_4$ ($LTB_4$), platelet activating factor (PAF), transferrin, and cytokines (e.g., IL-1 and TNF). These mediators stimulate activation of neutrophils and/or endothelial cells leading to expression of important adhesion molecules, such as integrins and selectins that mediate neutrophil binding. The adhesion of neutrophil to activated endothelium leads to neutrophil activation. Activated neutrophils have enhanced adhesion properties and the cells are highly migratory. The cells are also chemotactic and phagocytic. It is largely through their phagocytic activity that neutrophils promote clearance of infectious organisms.

Causes of inflammation are generally categorized as either infectious or non-infectious. Infectious diseases involving bacteria and viruses and other parasites, are usually treated by drugs that directly attack the infectious organism, (e.g. antibiotics such as penicillin and sulfonamides).

Non-infectious diseases in which neutrophils play a role in tissue damage include gout, rheumatoid arthritis, immune vasculitis, neutrophil dermatoses, glomerulonephritis, inflammatory bowel disease, myocardial infarction, ARDS (adult respiratory distress syndrome), asthma, emphysema and malignant neoplasms. Millions of people each year in the U.S. are treated for the above conditions. There are currently only a limited number of treatments for these chronic diseases which are usually characterized by long term morbidity and disability.

There can also be negative aspects to cytokine-mediated cell activation. The longer that activated neutrophils survive, the longer they continue to release enzymes and inflammatory mediators that can cause potentially harmful side effects. Though the half-life of circulating neutrophils is 6–8 hours, the extravascular survival of the activated cells can approach four days. Since it is well established that the numbers of activated neutrophils and their degree of activation is directly related to tissue injury, a tremendous amount of research has been done to identify compounds that inhibit the neutrophil response or that can decrease the number of activated neutrophils.

In vivo, as neutrophils die, they are recognized and phagocytosed by tissue macrophages, a process which is critical for resolution of the inflammatory response. In vitro, neutrophils undergo spontaneous apoptosis over a period of several days, which can be either enhanced or inhibited by cytokines and other mediators. Interestingly, phagocytosis of neutrophils was recognized by Metchnikoff over a hundred years ago (E. Metchnikoff, *Lecture VII. In Lectures on the comparative pathology of inflammation.* (F. A. Starling, ElH. Starling, eds.),; Kegan, Paul, Trench and Trubner [translated from French], 107–131, 1893). Phagocytosis of dying neutrophils is now recognized as the prime mode of resolving inflammation (J. Savill, *J. Leukoc. Biol.,* 61:375, 1997).

There are a number of factors that have been shown in vitro to slow the apoptosis of neutrophils. These include lipopolysaccharides derived from bacteria and lineage-specific cytokines such as granulocyte-macrophage colony-stimulating factor and glucocorticoids. The inhibition of apoptosis by these agents may be advantageous in that the neutrophils are allowed to live longer and scavenge microorganisms. This also allows time for monocytes to differentiate and become effective against the infectious organisms. Conversely, neutrophil apoptosis is known to be accelerated by ligation of the cell surface death receptor Fas to the Fas ligand (K. Iwai, T. Miyawaki, T. Takizawa, A. Koono, K. Ohta, A. Yachie et al., *Blood,* 84:1201, 1994; W. C. Liles, P. A. Kiener, J. A. Ledbetter, A. Aruffo, S. J. Klebanoff, *J. Exp. Med.,* 184:429, 1996), phagocytosis of bacteria (R. W. G. Watson, H. P. Redmond, J. H. Wang, C. Condron, D. Bouchier-Hayes, *Escherichia coli. Journal of Immunology*, 156:3986, 1996), and the binding of targets for the neutrophil integrin Mac-1 (A. Coxon, F. J. Barkalow, S. Askari, P. Rieu, A. H. Sharpe, U. Von-Andrian et al., *J. Leukoc. Biol.* (Suppl.) 64, 1996).

Work prior to the present invention has been directed toward identification of compounds that can control or regulate the inflammatory response. There are both chemically-derived drugs and bioactive proteins, termed cytokines, which have activity in regard to the inflammatory response. Chemical drugs used to treat inflammation are divided into two major classes, the steroidal and non-steroidal anti-inflammatory drugs. Steroidal anti-inflammatory drugs include the corticorsteroids, such as prednisone, methylprednisolone and cortisol. Non-steroidal anti-inflammatory drugs, the so-called NSAIDs, include aspirin, ibuprofen, indomethacin and diflunisal. In addition, tissues and blood cells release a variety of bioactive proteins, termed cytokines, that can have either anti- or pro-inflammatory activity. The pro-inflammatory mediators include IL-1, IL-8 and TNF-α and the anti-inflammatory proteins include IL-10. Another protein that indirectly has pro-inflammatory activity, and which is commercially produced by the biotechnology industry, is granulocyte-monocyte colony stimulating factor (GM-CSF). GM-CSF causes proliferation of neutrophils in the bone marrow and is used to treat patients undergoing chemotherapy who suffer from neutropenia (low neutrophil blood counts). A discussion of all these anti- and pro-inflammatory compounds can be found in *Internal Medicine*, Third Edition, (1990) by J. S. Stein, Editor-in-Chief, pp. 945–1239, Little Brown, Boston; and *Robbins Pathologic Basis of Disease*, Fourth Edition (1989) by R. S. Cotran, V. Dumar and S. L. Robbins, pp. 39–86, W. B. Saunders Co., Philadelphia.

In addition, as noted above, it is now known that the neutrophil adhesion to activated endothelium is a prerequisite for the inflammatory response. Proteins expressed by activated endothelium which are critical for neutrophil adhesion are selecting, such as P-selectin and E-selectin, and the immunoglobulin (Ig) superfamily members, such as CD54 (intercellular adhesion molecule-1 or ICAM-1). Neutrophils also express surface adhesion molecules, such as the β2 integrin LFA-1 (CD11a,b,c/CD18), which binds to ICAM-1, and L-selectin, which binds P-Selectin glycoprotein ligand-1 (PSGL-1) on already adherent neutrophils and heparan sulfate-related molecules on activated endothelial cells. However, of paramount importance to the initial steps in inflammation, is the adhesion of neutrophils to selecting on endothelial cells. The general roles of adhesion molecules in inflammation are discussed in "The Sensation and Regulation of Interactions within the Extracellular Environment: The Cell Biology of Lymphocyte Adhesion Receptors" (1990) by T. A. Springer, in the *Annual Review of Cell Biology*, Vol. 6:359–402.

Galectin-1 is just one of a family of related proteins, termed the galectin family of β-galactoside-binding proteins (see "Galectins: A Family of Animal β-Galactoside-Binding Lectins" (1994) by S. H. Barondes, V. Castronovo, D. N. W. Cooper, R. D. Cummings, K. Drickamer, et al., *In Cell* 76, 597–598). The known proteins are galectin-1 through -8. Galectins 1,2,4,6,7, and 8 are divalent. Galectins 1, 2 and 7 probably occur in a monomer⇌dimer equilibrium; however, only galectin-1 has been truly shown to undergo this equilibrium, ("Galectin-1, a β-Galactoside-Binding Lectin in Chinese Hamster Ovary Cells: I Physical and Chemical Characterization" (1995) by M.-J Cho and R. D. Cummings in the *Journal of Biological Chemistry* 270, 5198–5206). Galectins 4, 6, and 8 are covalent dimers and can only exist as dimers. In contrast, galectins 3 and 5 exist as monomeric species. Galectin-3 has been proposed to have an effect of blocking apoptosis of certain cells ("Expression of Galectin-3 Modulates T-cell Growth and Apoptosis" by R. Y. Yang, D. K. Hsu, and F. T. Liu (1996) in the *Proceedings of the National Academy of Sciences, United States of America* 93, 6737–42), though this has not been demonstrated for human neutrophils.

Galectin-1 forms a homodimer of 14 kDa subunits and each subunit has a single carbohydrate-binding site. This lectin is unusual in that it is synthesized in the cytosol of mammalian cells where it accumulates in a monomeric form. The lectin is actively, but slowly secreted ($t_{1/2} \approx 20$ h), and the secreted form occurs as a "metastable intermediate" that requires glycoconjugate ligands to properly fold and acquire stability. The functional lectin exists in a monomer-dimer equilibrium with a $K_d$ of ~7 μM and the equilibrium rate is rather slow ($t_{1/2} \approx 10$ h).

Several known cytokines have been proposed to have carbohydrate binding activity and galectins, such as galectin-1, may antagonize or promote their activities. Recently, it was shown that galectin-1 can cause death of T-lymphocytes ("Apoptosis of T Cells Mediated By Galectin-1" (1995) by N. L. Perillo, K. E. Pace, J. J. Seilhamer, and L. G. Baum, *Nature* 378, 736–9). T cells stimulated by antigen, but not resting T cells, were killed apoptotically by galectin-1. Perillo, et al., speculated that this apoptosis required the dimeric form of the lectin, but no direct evidence was presented for this idea. Furthermore, they did not define any specific changes in cell surface glycoconjugates accompanying T cell activation that might predispose T cells to die by apoptosis. Indeed, Perillo et al. stated that resting T cells bind galectin-1, but are not killed.

Galectin-1 has been used in therapeutic treatments for T cell-based autoimmune diseases in animal models; for example, experimental autoimmune encephalomyelitis (H. Offner, B. Celnik, T. S. Bringman, D. Casentini-Borocz, G. E. Nedwin, A. A. Vandenbark, Recombinant Human Beta-galactoside Binding Lectin Suppresses Clinical and Histological Signs of Experimental Autoimmune Encephalomyelitis, *Journal of Neuroimmunology*, 28(2):84, 1990), and experimental autoimmune myasthenia gravis (G. Levi, R. Tarrab-Hazdai, V. I. Teichberg, Prevention and Therapy with Electrolectin of Experimental Autoimmune Myasthenia Gravis in Rabbits, *European Journal of Immunology*, 13(6):7, 1983).

Galectin-1 can inhibit the growth of certain types of cells ("Identification of an Autocrine Negative Growth Factor: Mouse Beta-Galactoside-Binding Protein is a Cytostatic Factor and Cell Growth Regulator" (1991) V. Wells and L. Mallucci, *Cell* 64, 91–7). However, the specific findings regarding the effects of galectin-1 on activated neutrophils demonstrated herein are unanticipated by previous studies. Indeed, as noted above, resting T-cells bind galectin-1 but are not killed by this binding.

As indicated above, acute inflammatory reactions are often initiated by invasive organisms and injury; however, there are many other disease states characterized by acute inflammation.

It is with this in mind that physicians attempt to control the acute inflammatory reaction with glucocorticoids, non-steroidal anti-inflammatory agents and cytotoxic drugs. These general immunosuppressive agents are helpful but are not specifically directed to the resolution of the acute inflammatory response. Agents specifically directed to the control of the acute reaction would be less likely to promote the systemic side effects produced by general immunosuppressives and would permit better control over a potentially life-threatening reaction. Effective inhibitors of causative factors of the acute inflammation which have fewer side effects would therefore be most useful.

SUMMARY OF THE INVENTION

It has been discovered that galectin-1, a protein which normally resides in the blood vessel walls, is able to bind to activated neutrophils. This binding of galectin-1 to activated neutrophils causes the neutrophils to quickly die by a process termed apoptosis, or programmed cell death. It has been further discovered that upon activation of neutrophils, there are changes in the surface of the cells, which result in a loss of surface sialic acid and consequently, exposure of binding sites for galectin-1. It has also been discovered that this killing induced by galectin-1 requires the dimeric form of the protein (two non-covalently [or optionally-covalently] associated subunits). The monomeric form of galectin-1, on the other hand, can block the binding of the dimeric species and thereby inhibit apoptosis. Galectin-1 is a normal protein constituent of blood vessel walls. The fact that galectin-1 is a naturally occurring protein in the vascular bed makes it an ideal choice as a powerful inflammatory regulator. Because neutrophils become activated prior to diapedesis, they become susceptible to galectin-1-induced apoptosis before diapedesis. Thus, dimeric galectin-1, when placed in the circulation, has an anti-inflammatory effect, whereas the monomeric galectin-1 has a pro-inflammatory effect. It is one objective of the present invention to provide a composition which can be used therapeutically to inhibit neutrophils when an anti-inflammatory effect is desired or to inhibit apoptosis of neutrophils when a pro-inflammatory effect is desired. It is another objective of the invention to provide methods of screening for compounds able to mimic the action of galectin-1 on neutrophils.

BRIEF DESCRIPTION OF THE DRAWINGS

FIG. 4A shows a comparison of the abilities of the dimeric and monomeric forms of galectin-1 to induce apoptosis in desialylated HL-60 cells.

FIG. 4B shows the kinetics of induction of apoptosis in desialylated HL-60 cells by galectin-1 with and without lactose.

DETAILED DESCRIPTION OF THE INVENTION

The present invention is based on the discovery that the dimeric form of galectin-1 is able to bind to activated neutrophil cells and to induce apoptosis of the cells thereby acting as an anti-inflammatory agent. Further, it has been discovered that the monomeric form of galectin-1 blocks the binding of the dimeric form thereby inhibiting apoptosis of the neutrophils thereby acting as a pro-inflammatory agent. Where used herein treatment of inflammation refers to prophylaxis as well as treatment of an existing condition.

The factors regulating neutrophil apoptosis are poorly understood. To explore these factors, the changes in neutrophil surfaces that accompany activation and which might prime the cells to respond to apoptotic stimuli were examined.

Whether or not the loss of surface sialic acid accompanying neutrophil activation might enhance interactions of the cells with naturally occurring lectins in the vascular bed that recognize penultimate and/or internal galactosyl residues in glycans for recognition were explored. Sialic acids on cell surfaces are most often linked to galactosyl residues. Galectin-1 can also interact with polylactosamine sequences containing the repeating disaccharide $[\rightarrow 3Gal\beta 1 \rightarrow 4GlcNAc\beta 1 \rightarrow]_n$. Sialylation of short polylactosamines blocks recognition by the galectin-1.

Methodology and Results

Figure 1:
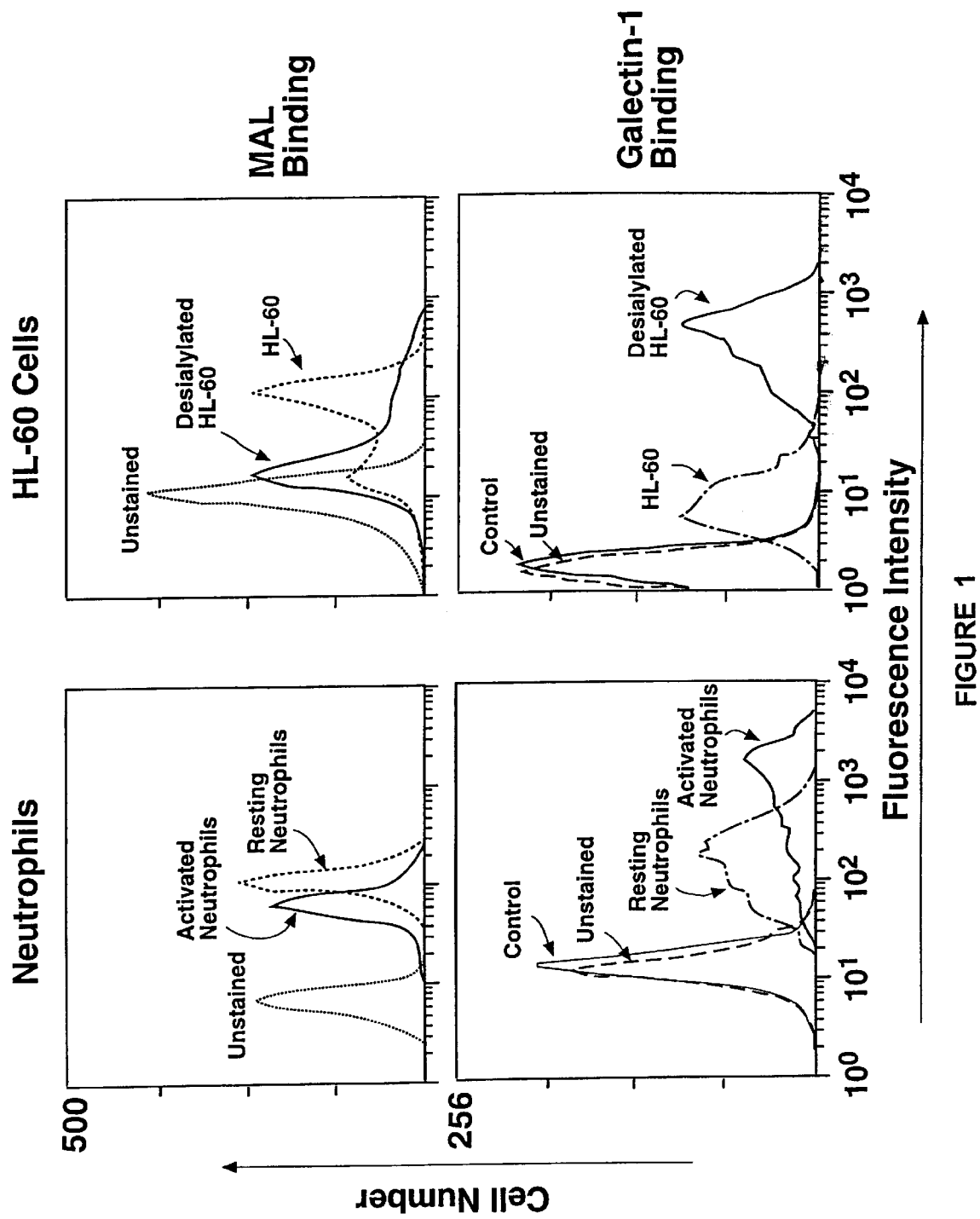
FIG. 1 shows the binding of galectin-1 and *Maackia amurensis* leukoagglutinin (MAL) to activated and resting to neutrophils and to normal and desialylated HL-60 cells.

As shown in FIG. 1, activation of neutrophils decreases surface sialic acid, increases galectin-1 binding, and decreases binding by MAL (*Maackia amurensis* leukoagglutinin). Isolated neutrophils were activated by treatment with PMA and HL-60 cells were desialylated by treatment with neuraminidase. Heparinized blood was obtained from normal donors. Neutrophils were isolated by dextran sedimentation, hypotonic lysis, and density gradient centrifugation on HISTOPAQUE-1077 (Sigma), as described [G. A. Zimmerman, T. M. McIntyre, and S. M. Prescott, *J. Clin. Invest.*, 76:2235, 1985]. Typically, the polymorphonuclear cells were >90% neutrophils by Wright-Giemsa staining and >90% CD16$^+$ as assessed by flow cytometry. Neutrophils were activated by treatment with phorbol myristate acetate (PMA) (Sigma) (0.5 μM) for 20 minutes at 37° C. in RPMI containing 20% FCS (0.5 ml). HL-60 cells were routinely maintained in RPMI containing 20% FCS. Desialylated HL-60 cells were prepared by treating 3×10$^7$ cells with *Arthrobacter ureafaciens* neuraminidase (Sigma) (100 mU) in 500 μl of RPMI containing 20% FCS for 1 hour at 37° C. Cells were washed twice with RPMI before use. Cells were incubated with biotinylated-MAL (10 μg/ml) or recombinant, biotinylated-galectin-1 (10 μg/ml) for 30 minutes on ice and washed once with PBS. The washed cells were incubated with FITC-streptavidin (1:100 dilution) (Sigma), washed once with PBS, and analyzed by flow cytometry. Recombinant galectin-1 was prepared and biotinylated as described in M. Cho and R. D. Cummings, *J. Biol. Chem.*, 270:5198, 1995; and, *J. Biol. Chem.*, 270:5207, 1995. This protein contains a stabilizing mutation in which Cys at the 2nd residue was converted to Ser. The mutated monomeric form of galectin-1, termed N-Gal-1, was prepared as described in M. Cho and R. D. Cummings, *Biochemistry*, 35:13081, 1996. "Unstained" indicates fluorescence of either resting neutrophils or HL-60 cells incubated in the absence of either MAL or galectin-1. "Control" indicates fluorescence of either activated neutrophils or desialylated HL-60 cells incubated with galectin-1 in the presence of 10 mM lactose.

As shown herein, activation of neutrophils by phorbol myristate (PMA) substantially enhances their binding to galectin-1 (FIG. 1). In addition, desialylation of HL-60 cells by neuraminidase treatment enhances their binding to galectin-1 (FIG. 1).

Activated cells were also found to lose binding sites for the sialic acid-binding plant lectins, *Maackia amurensis* leukoagglutinin (MAL) and *Sambucus nigra* agglutinin (SNA) (data not shown). MAL binds to sialylated glycoconjugates with the sequence NeuAcα2→3Galβ1→4GlcNAc→R and SNA binds to sialylated molecules with the sequence NeuAcα2→6Gal/GalNAc→R (W. C. Wang and R. D. Cummings, *J. Biol. Chem.*, 263:4576, 1988; N. Shibuya, I. J. Goldstein, W. F. Broekaert, M. Nsimba-Lubaki, B. Peeters, and W. J. Peumans, *J. Biol. Chem.*, 262:1596, 1987). Thus, activation of neutrophils decreases the level of surface sialic acid. These results are consistent with prior evidence that activation of neutrophils mobilizes a neuraminidase from intracellular stores to the exterior of the cells, resulting in the release of sialic acid (A. S. Cross and D. G. Wright, *J. Clin. Invest.*, 88:2067, 1993). In related experiments, we examined the binding of MAL and SNA to HL-60 cells, a human promyelocytic leukemic cell line. HL-60 cells share many surface markers with neutrophils and are often used as an in vitro model of neutrophils, although HL-60 cells cannot undergo activation. HL-60 cells bind both MAL (FIG. 1) and SNA (data not shown), whereas HL-60 cells desialylated by neuraminidase treatment bind less MAL (FIG. 1) and SNA (data not shown).

In all cases cell binding of galectin-1 to cells was inhibited by 10 mM lactose, a known inhibitor of galectin-1 (FIG. 1), but not by 10 mM maltose, an isomeric, non-inhibitory analog (data not shown). We noted that both activated neutrophils and desialylated HL-60 cells are strongly agglutinated by galectin-1, whereas resting neutrophils and HL-60 cells are not appreciably agglutinated, which further underscores the profound differences in surface phenotypes between resting and activated neutrophils. These results demonstrate that neutrophil activation induces surface desialylation and exposes galactose-containing ligands for galectin-1.

Figure 2A:
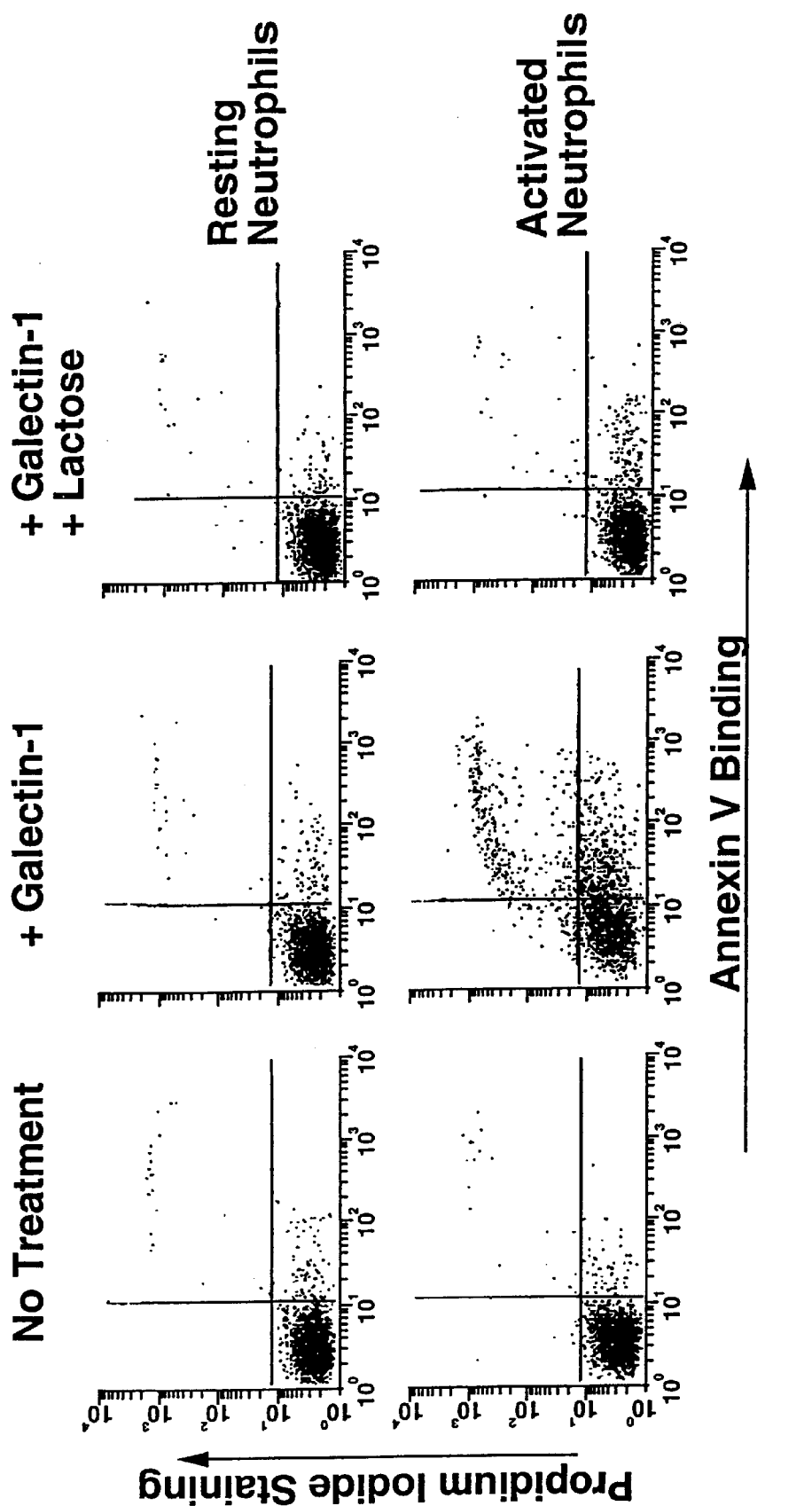
FIG. 2A shows that galectin-1 induces the apoptosis of activated neutrophils as indicated by the increased binding to annexin V.
Figure 2B:
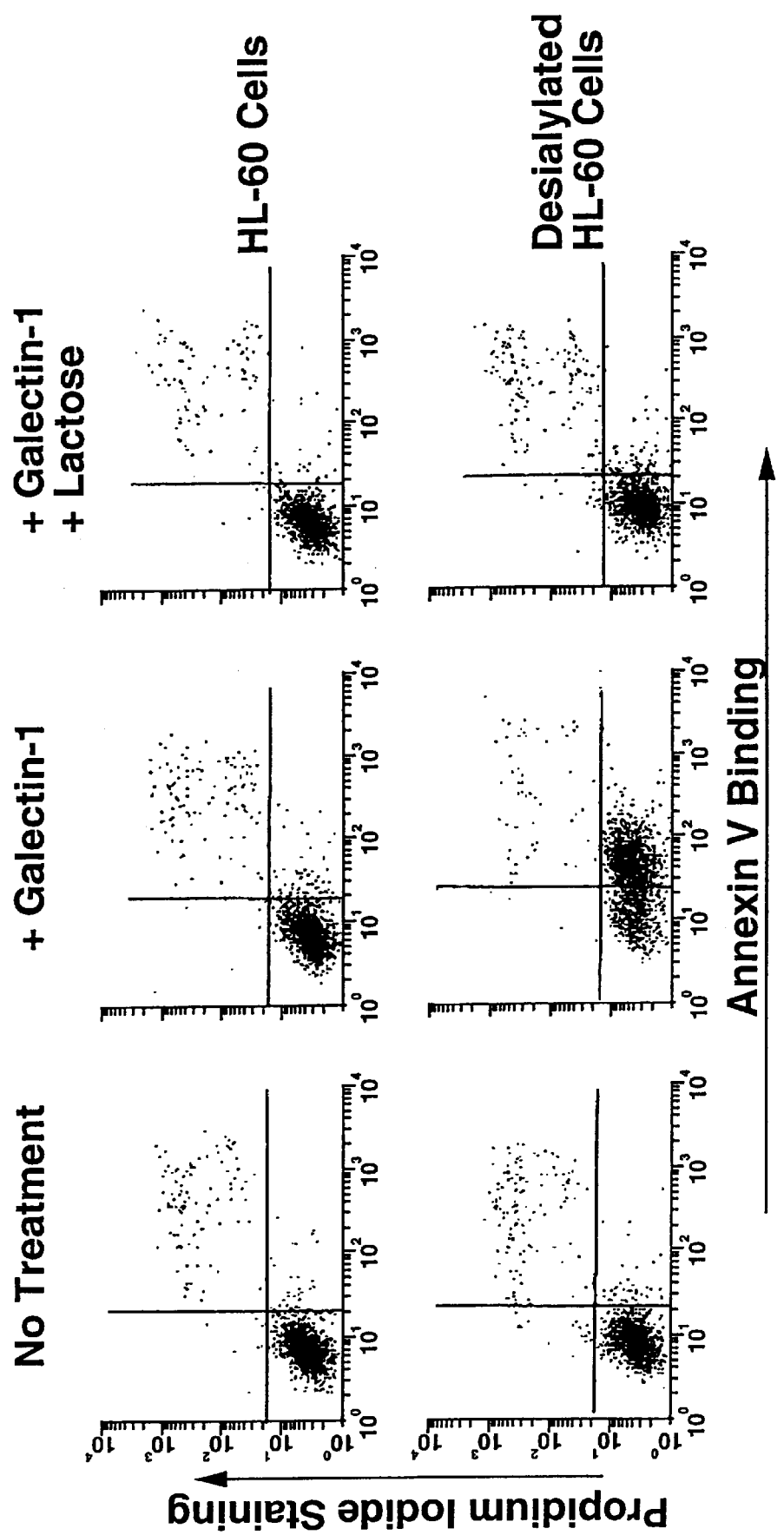
FIG. 2B shows that galectin-1 induces the apoptosis of desialylated HL-60 cells as indicated by the increased binding to annexin V.

The binding of galectin-1 to activated neutrophils and to desialylated HL-60 cells results in cell death by apoptosis, as measured by binding of the unpermeabilized cells to annexin V (FIGS. 2A and 2B).

Resting or activated neutrophils ($3\times10^6$ cells) were treated with galectin-1 (10 $\mu$M) in 0.5 ml of HBSS (lacking $Ca^{2+}$/$Mg^{2+}$ and containing 0.5% human albumin) for 90 minutes at 37° C. in the presence or absence of 10 mM lactose. HL-60 cells and desialylated HL-60 cells ($3\times10^6$ cells/0.5 ml) were treated with galectin-1 (10 $\mu$M) for 20 hours at 37° C. in the presence or absence of 10 mM lactose. At the end of the incubations all cells were treated with 10 mM lactose in PBS to disaggregate the cells. Cells were washed once with PBS and the cells were stained with a mixture of FITC-conjugated annexin V (Boehringer Mannheim), to assess apoptosis, and with propidium iodide (1 $\mu$g/ml) (Molecular Probes), to assess cell viability.

Annexin V is a protein that recognizes phosphatidyl serine (PS) and is a convenient marker for apoptosis of neutrophils and other cells (S. J. Martin, C. P. Reutelingsperger, A. J. McGahon, J. A. Rader, R. C. van Schie, D. M. LaFace and D. R. Green DR, *J. Exp. Med.*, 182:1545, 1995; C. H. Homburg, M. de Haas, A. E. von dem Borne, A. J. Verhoeven, C. P. Reutelingsperger and D. Roos, *Blood*, 85:532, 1995; I. Vermes, C. Haanen, H. Steffens-Nakken, and C. Reutelingsperger, *J. Immunol. Methods*, 184:39, 1995; Z. Darzynkiewicz, G. Juan, X. Li, W. Gorczyca, T. Murakami, and F. Traganos, *Cytometry* 27:1, 1997). PS is normally concentrated on the inner leaflet of the plasma membrane, but it is repositioned to the outer leaflet in apoptotic cells (see citations immediately above). The function of this repositioning may be to trigger macrophage recognition of dying cells (V. A. Fadok, J. S. Savill, C. Haslett, D. L. Bratoon, D. E. Doherty, P. A. Campbell and P. M. Henson, *J. Immunol.*, 149:4029, 1992). To assess their integrity, cells were also treated with propidium iodide (PI), a membrane-impermeable DNA-binding dye that can only enter cells in which the membrane has been compromised. Within 90 minutes following treatment with 10 $\mu$M galectin-1, 36% of the activated neutrophils undergo apoptosis, as determined by their staining with annexin V (FIG. 2A). Some of these cells (~16% of the total) are stained with both annexin V and PI (FIG. 2A). This latter group of double-staining cells are probably undergoing accelerated apoptosis resulting in cell leakiness. In contrast, galectin-1 does not induce annexin V or PI staining of resting neutrophils (<10% of the cells stained with annexin V or annexin V and PI). Similar results were obtained for desialylated HL-60 cells, with approximately 65% of the cells undergoing apoptosis upon treatment with 10 $\mu$M galectin-1 (FIG. 2B). The non-desialylated HL-60 cells do not undergo appreciable apoptosis upon treatment with galectin-1. Both the apoptosis-inducing and cell agglutinating activities of galectin-1 are inhibited by lactose, but not by maltose.

In seeking to better understand the oligomeric structure of galectin-1 in solution, a series of physico-chemical studies of the recombinant form of CHO cell galectin-1 produced in *E. coli* was performed. Unexpectedly, galectin-1 was found to be a monomer that could reversibly associate to form a dimer with a $K_d$ for dimer formation of ~7 $\mu$M (Cho and Cummings, 1995b, *J. Biol. Chem.*, 270:5198–5206). Interestingly, the equilibration time between monomeric and dimeric forms was relatively slow ($t_{1/2}\approx10$ h). We also studied the form of galectin-1 in the cytosol of the mutant Lec8 CHO cells immediately following extraction of the cells. The cytosolic form of the lectin was mostly monomeric, but some dimeric forms were also detected (Cho and Cummings, 1995b, *J. Biol. Chem.*, 270:5198–5206).

To investigate whether dimerization of the galectin-1 is required to induce apoptosis, mutated forms of galectin-1 were prepared. Recombinant hamster galectin-1, which is highly homologous in sequence with bovine and human galectin-1 with 100% identity at the N- and C-termini positions was used. The protein was prepared as described in Cho and Cummings, 1995b, *J. Biol. Chem.*, 270:5198–5206, ibid, *J. Biolchem*, 270:5207, 1995. This protein (monomeric or dimeric) contains a stabilizing mutation (monomeric or dimeric) in which Cys at the 2nd residue was converted to Ser.

Figure 3:
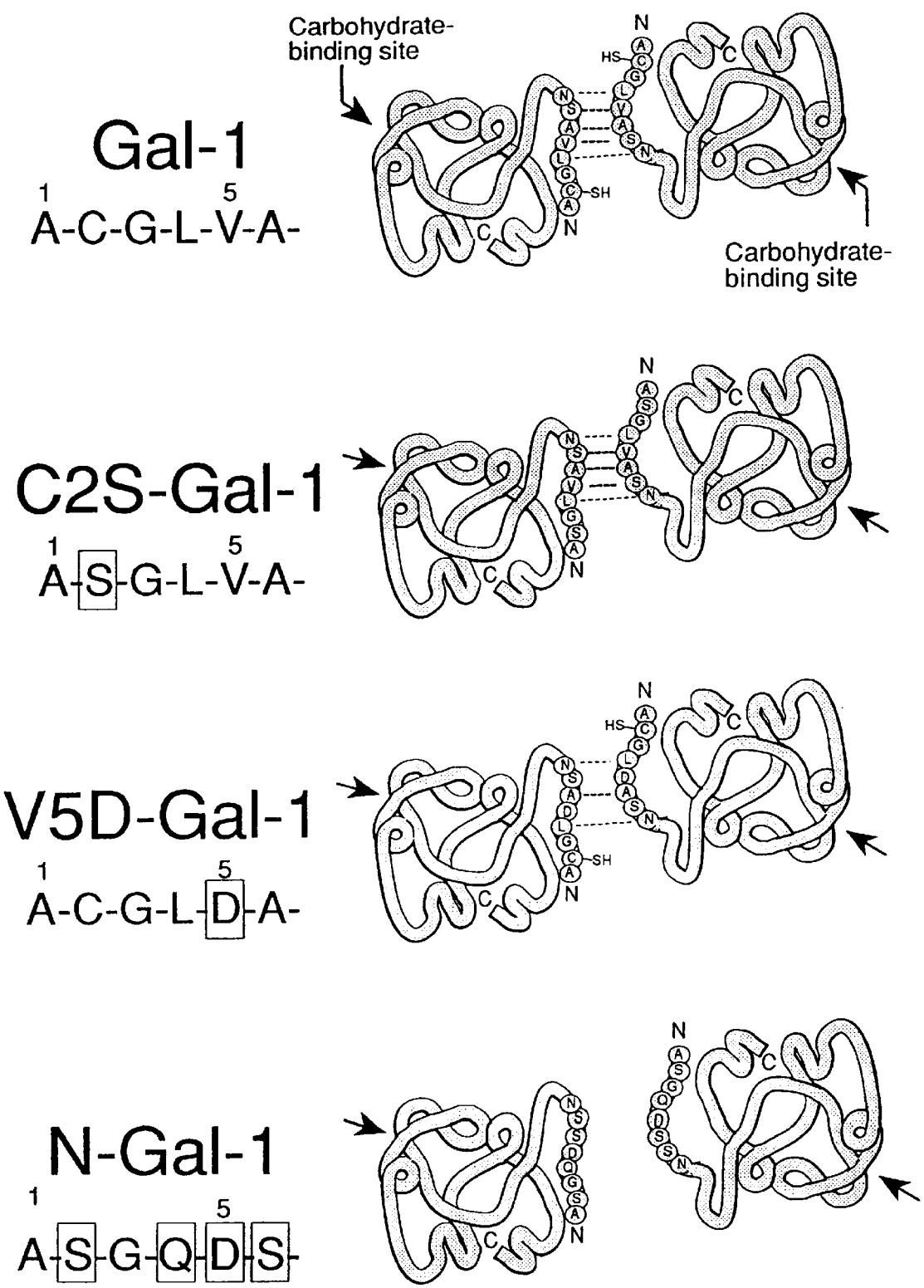
FIG. 3 shows molecular versions of several mutant forms of galectin-1.

Specific mutations were created in the six N-terminal amino acid (SEQ ID NO:1) of hamster galectin-1, as indicated in FIG. 3 and as described in further detail in Cho and Cummings, *Biochemistry*, 35:13081, 1996, which is hereby incorporated by reference herein in its entirety. C2S-Gal-1 (SEQ ID NO:2) contains a single replacement of Cys-2 to Ser. V5D-Gal-1 (SEQ ID NO:3) contains a single mutation of Val-5 to Asp. N-Gal-1 (SEQ ID NO:4) contains disruptions of three hydrophobic amino acids at the N-terminus. We also made another mutant construct, termed N/C-Gal-1, which contained the amino terminal changes of N-Gal-1 in addition to multiple changes in specific hydrophobic amino acids at the C-terminus (data not shown). All mutants, except for C2S-Gal-1, behaved as monomers in size exclusion HPLC and native gel electrophoresis. C2S-Gal-1 was indistinguishable from the native lectin in its ability to undergo monomer-dimer equilibrium and in its carbohydrate-binding affinity. N-Gal-1 and V5D-Gal-1 were found to bind weakly to lactosyl-SEPHAROSE, compared to C2S-Gal-1 and native Gal-1, which bound tightly to the column. However, in equilibrium dialysis N-Gal-1 and V5D-Gal-1 bound N-acetyllactosamine with similar affinity ($K_d \approx 90$ μM) to that of the C2S-Gal-1 and the native lectin. Thus, the monomeric form of the lectin exhibits much lower affinity for complex carbohydrate ligands, such as glycoproteins, than the dimeric forms. N/C-Gal-1 was non-functional.

Although both V5D-Gal-1 and N-Gal-1 behaved as monomers rather than dimers at low lectin concentrations, the lectins were able to dimerize at high concentrations and could be covalently cross-linked with disuccinimidyl suberate. The $K_d$ of monomer-dimer equilibrium for V5D-Gal-1 and N-Gal-1 was estimated to be 60 μM and ≈250 μM, respectively. VSD-Gal-1 had a high rate of dissociation compared to C2S-Gal-1 or native galectin-1. The cross-linked dimers of V5D and N-Gal-1 were highly active in binding carbohydrate and were similar to both C2S-Gal-1 and the native lectin in both hemagglutinating activity and high affinity binding to lactosyl-Sepharose.

These results demonstrate that monomeric and dimeric forms of galectin-1 can be created and indicate that the dimeric lectin can be covalently cross-linked to generate a highly functional and stable lectin. The tight binding of the cross-linked dimeric N-Gal-1 to lactosyl-Sepharose, compared to the weak binding of monomeric N-Gal-1, demonstrate that dimerization is critical for high affinity binding to macromolecular ligands.

In N-Gal-1 specific hydrophobic amino acid residues in the N-terminal subunit interface were substituted with hydrophilic residues (see Cho and Cummings, 1996). N-Gal-1 is mostly monomeric at concentrations of 200 μM, but it is similar to galectin-1 in its specificity and affinity for galactose-containing glycans.

The ability of the dimeric and monomeric forms of galectin-1 to induce apoptosis were studied for desialylated HL-60 cells as shown in FIGS. 4A and 4B. In FIG. 4A, the apoptosis of desialylated HL-60 cells was measured (as described above in FIGS. 2A and 2B), without treatment by galectin-1, in the presence of galectin-1 (10 μM), or in the presence of monomeric galectin-1 (20 μM, N-Gal-1). In FIG. 4B, desialylated HL-60 cells were exposed to 10 μM galectin-1 for indicated times before addition of 10 mM lactose to inhibit the lectin binding. Cells were incubated at 37° C. in RPMI containing 20% FCS for up to 20 hours. The percent of apoptotic cells is taken as that percent of the cells staining positively with FITC-conjugated annexin V, as shown previously in FIG. 2B. Desialylated HL-60 cells treated with the indicated concentrations of galectin-1 were incubated for 20 hours at 37° C., and apoptosis was measured as described above. HL-60 cells were treated with the indicated amounts of neuraminidase for 1 hour at 37° C., washed with RPMI, and then incubated with galectin-1 (10 μM) for 20 hours at 37° C. in RPMI containing 20% FCS. Apoptosis was analyzed as described above.

As shown in FIG. 4A, the monomeric N-Gal-1, even at a concentration of 20 μM, does not significantly induce apoptosis of desialylated HL-60 cells. Treatment with dimeric galectin-1 causes 59.5% of the cells to undergo apoptosis (FIG. 4A), whereas only 7.9% of the cells treated with N-Gal-1 (monomeric galectin-1) undergo apoptosis compared to 3.8% for untreated cells (FIG. 4A). It is concluded that N-Gal-1 is able to bind to the cells, since it blocks agglutination by dimeric galectin-1 (data not shown). These results demonstrate that the dimeric form of galectin-1 is required for its apoptotic activity.

Half-maximal apoptosis of the cells is observed within 2–3 hours following treatment (FIG. 4B) and requires approximately 10 μM galectin-1 (FIG. 4B). The induction of apoptosis is dependent upon neuraminidase treatment of the cells (FIG. 4B). The concentration of galectin-1 required to induce apoptosis is just above the $K_d$ for monomer$\leftrightarrow$dimer equilibrium, which is consistent with the evidence above that dimerization is required for inducing apoptosis. The galectin-1 concentrations that induce apoptosis and the kinetics of apoptosis induction in enzymatically desialylated HL-60 cells are similar to those observed for activated neutrophils.

Galectin-1 induces apoptosis of immature thymocytes, with a half-maximal effect at a lectin concentration of ~10 μM (N. L. Perillo, K. E. Pace, J. J. Seilhamer, and L. G. Baum, Nature, 378:736, 1995), consistent with the observation that only the dimeric form of the lectin has apoptosis-inducing activity. Interestingly, galectin-3, which is exclusively monomeric, inhibits apoptosis in T-cell lines overexpressing the protein; expression of the protein also correlates with cellular transformation.

Activation of neutrophils causes mobilization, redistribution, or proteolytic shedding of a variety of surface glycoproteins. In addition, activation mobilizes a neuraminidase from intracellular granules to the exterior of the cells. Our data indicate that a critical function of this redistributed neuraminidase is to expose polylactosamine ligands for galectin-1, which the activated neutrophils encounter after they emigrate into perivascular tissues at sites of inflammation. Emigrating neutrophils may also encounter other factors that regulate apoptosis, such as glucocorticoids, granulocyte-monocyte colony stimulating factor and interleukin-6 that inhibit apoptosis and tumor necrosis factor-α and heparin that promote apoptosis. Human neutrophils also express Fas, a surface glycoprotein, and its secreted ligand FasL; ligation of Fas by anti-Fas IgM promotes apoptosis of neutrophils (W. C. Liles, P. A. Kiener, J. A. Ledbetter, A. Aruffo and S. J. Klebanoff, J. Exp. Med., 184:429 1996).

The compositions used in the methods described herein comprise purified dimeric or monomeric forms of galectin-1 or mutants or functional derivatives thereof as explained in further detail below.

Utility

The present invention provides a method for the treatment of a patient afflicted with inflammatory diseases wherein such disease states may be treated by the administration of an effective amount of a compound of the present invention to a patient in need thereof. The present invention further provides a method of treating a patient to promote an inflammatory response by treating the patient with an effective amount of a compound of the present invention.

A therapeutically effective amount of a compound of the present invention refers to an amount which is effective in controlling, reducing, or promoting the inflammatory response. The term "controlling" is intended to refer to all processes wherein there may be a slowing, interrupting, arresting, or stopping of the progression of the disease and does not necessarily indicate a total elimination of all disease symptoms. Where used herein, the term "purified" galectin-1 refers to galectin-1 (monomeric or dimeric form) which is substantially free of natural contaminants.

The term "therapeutically effective amount" is further meant to define an amount resulting in the improvement of any parameters or clinical symptoms characteristic of the inflammatory response. The actual dose will be different for the various specific molecules, and will vary with the patient's overall condition, the seriousness of the symptoms, and counterindications.

As used herein, the term "subject" or "patient" refers to a warm blooded animal such as a mammal which is afflicted with a particular inflammatory disease state. It is understood that guinea pigs, dogs, cats, rats, mice, horses, cattle, sheep, and humans are examples of animals within the scope of the meaning of the term.

A therapeutically effective amount of the compound used in the treatment described herein can be readily determined by the attending diagnostician, as one skilled in the art, by the use of conventional techniques and by observing results obtained under analogous circumstances. In determining the therapeutically effective dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristic of the preparation administered; the dose regimen selected; the use of concomitant medication; and other relevant circumstances.

A therapeutically effective amount of the compositions of the present invention will generally contain sufficient active ingredient to deliver from about 0.1 $\mu$g/kg to about 50 mg/kg (weight of active ingredient/body weight of patient). Preferably, the composition will deliver at least 0.5 to 10 mg/kg, and more preferably at least 1 $\mu$g/kg to 1 mg/kg. The foregoing amounts apply both to the dimeric and monomeric forms of galectin-1.

Practice of the method of the present invention comprises administering to a patient a therapeutically effective amount of the active ingredient(s), in any suitable systemic or local formulation, in an amount effective to deliver the dosages listed above. An effective, particularly preferred dosage of the dimeric form of galectin-1 for substantially inhibiting activated neutrophils is 1 $\mu$g/kg to 1 mg/kg. The dosage can be administered on a one-time basis, or (for example) from one to 5 times per day. Alternatively, the monomeric form of galectin-1 can be used in a purified form to inhibit apoptosis of neutrophil cells.

Preferred amounts and modes of administration are able to be determined by one skilled in the art. One skilled in the art of preparing formulations can readily select the proper form and mode of administration depending upon the particular characteristics of the compound selected the disease state to be treated, the stage of the disease, and other relevant circumstances using formulation technology known in the art, described for example in *Remington's Pharmaceutical Sciences*, latest edition, Mack Publishing Co.

Pharmaceutical compositions can be manufactured utilizing techniques known in the art. Typically the therapeutically effective amount of the compound will be admixed with a pharmaceutically acceptable carrier.

The compounds or compositions of the present invention may be administered by a variety of routes, for example, orally or parenterally (i.e. subcutaneously, intravenously, intramuscularly, intraperitoneally, or intratracheally).

For oral administration, the compounds can be formulated into solid or liquid preparations such as capsules, pills, tablets, lozenges, melts, powders, suspensions, or emulsions. Solid unit dosage forms can be capsules of the ordinary gelatin type containing for example, surfactants, lubricants and inert fillers such as lactose, sucrose, and cornstarch or they can be sustained release preparations.

In another embodiment, the compounds of this invention can be tabletted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, and buffers as are known in the art.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

As noted above, the compositions can also include an appropriate carrier. For topical use, any of the conventional excipients may be added to formulate the active ingredients into a lotion, ointment, powder, cream, spray, or aerosol. For surgical implantation, the active ingredients may be combined with any of the well-known biodegradable and bio-erodible carriers, such as polylactic acid and collagen formulations. Such materials may be in the form of solid implants, sutures, sponges, wound dressings, and the like. In any event, for local use of the materials, the active ingredients usually be present in the carrier or excipient in a weight ratio of from about 1:1000 to 1:20,00, but are not limited to ratios within this range. Preparation of compositions for local use are detailed in *Remington's Pharmaceutical Sciences*, latest edition, (Mack Publishing).

Additional pharmaceutical methods may be employed to control the duration of action. Controlled release preparations may be achieved through the use of polymers to complex or absorb galectin-1 or its functional derivatives. The controlled delivery may be achieved by selecting appropriate macromolecules (for example, polyesters, polyamino acids, polyvinyl, pyrrolidone, ethylenevinylacetate, methylcellulose, carboxymethylcellulose, or protamine, sulfate) and the appropriate concentration of macromolecules as well as the methods of incorporation, in order to control release.

Another possible method useful in controlling the duration of action by controlled release preparations is incorporation of the galectin-1 molecule or its functional derivatives into particles of a polymeric material such as polyesters, polyamino acids, hydrogels, poly(lactic acid), or ethylene vinylacetate copolymers.

Alternatively, instead of incorporating galectin-1 or its functional derivatives into polymeric particles, it is possible to entrap these materials in microcapsules prepared, for example, by coacervation techniques or by interfacial polymerization (for example, hydroxymethylcellulose or gelatine-microcapsules and poly(methylmethacylate) microcapsules, respectively), in colloidal drug delivery systems (for example, liposomes, albumin microspheres, microemulsions, nano-particles, and nanocapsules), or in macroemulsions. Such techniques are disclosed in the latest edition of *Remington's Pharmaceutical Sciences*.

U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A good review of known methods is by G. Gregoriadis, Chapter 14. "Liposomes", *Drug Carriers in Biology and Medicine*, pp. 287–341 (Academic Press, 1979). Microspheres formed of polymers or proteins are well known to those skilled in the art, and can be tailored for passage through the gastrointestinal tract directly into the blood stream. Alternatively, the agents can be incorporated and the microspheres, or composite of microspheres, implanted for slow release over a period of time, ranging from days to months. See, for example, U.S. Pat. Nos. 4,906,474, 4,925,673, and 3,625,214.

When the composition is to be used as an injectable material, it can be formulated into a conventional injectable carrier. Suitable carriers include biocompatible and pharmaceutically acceptable phosphate buffered saline solutions, which are preferably isotonic.

As an atomizable composition, or a lavage, the active ingredients of the present invention may be administered to treat diseases of the lungs. Diseases of the lungs involving inflammation include asbestosis, silicosis, coal miner's pneumoconiosis; those relating to autoimmune conditions that may involve the lungs include rheumatoid arthritis, lupus erythematosus; and granulomatous inflammations of the lungs include Wegener's granulomatosis and eosinophilic granulomatosis.

The term "inflammation" is meant to include reactions of both the specific and non-specific defense systems. A specific defense system reaction is a specific immune system reaction response to an antigen. Examples of a specific defense system reaction include the antibody response to antigens such as rubella virus, and delayed-type hypersensitivity response mediated by T-cells (as seen, for example, in individuals who test "positive" in the Mantaux test).

A non-specific defense system reaction is an inflammatory response mediated by leukocytes incapable of immunological memory. Such cells include granulocytes, macrophages, neutrophils, etc. Examples of a non-specific defense system reaction include the immediate swelling at the site of a bee sting, the reddening and cellular infiltrate induced at the site of a burn and the collection of PMN leukocytes at sites of bacterial infection (e.g., pulmonary infiltrates in bacterial pneumonias, pus formation in abscesses).

Although the invention is particularly suitable for cases of acute inflammation, it also has utility for chronic inflammation. Types of inflammation that can be treated with the present invention include diffuse inflammation, traumatic inflammation, immunosuppression, toxic inflammation, specific inflammation, reactive inflammation, parenchymatous inflammation, obliterative inflammation, interstitial inflammation, croupous inflammation, and focal inflammation.

It will be appreciated that the present invention will be easily adapted to the diagnosis, monitoring, and treatment of inflammatory disease processes such as rheumatoid arthritis, acute and chronic inflammation, post-ischemic (reperfusion) leukocyte-mediated tissue damage, acute leukocyte-mediated lung injury (e.g., Adult Respiratory Distress Syndrome), and other tissue-or organ-specific forms of acute inflammation (e.g., glomerulonephritis).

Where used herein, the term "functional derivatives" is intended to include the "fragments," "variants," "analogues," or "chemical derivatives" of the subject polypeptides. A "fragment" of galectin-1 polypeptide is meant to refer to a polypeptide subset. A "variant" of the polypeptides is meant to refer to naturally occurring molecules substantially similar to either the entire molecules or fragments thereof. An "analogue" of galectin-1 is meant to refer to a non-natural molecule substantially similar to either the entire molecules or fragments thereof or a molecule which has the same apoptotic inducing activity as galectin-1.

A molecule is said to be "substantially similar" to another molecule if the sequence of amino acids in both molecules is substantially the same, and if both molecules possess a similar biological activity. Thus, provided that two molecules possess a similar activity, they are considered variants as that term is used herein even if one of the molecules contains additional amino acid residues not found in the other, or if the sequence of amino acid residues is not identical.

As used herein, a molecule is said to be a "chemical derivative" of another molecule when it contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Examples of moieties capable of mediating such effects are disclosed in the latest edition of *Remington's Pharmaceutical Sciences*, and will be apparent to those of ordinary skill in the art.

A suitable screening method for determining whether a given compound is a galectin-1 functional derivative comprises, for s example, bioassays as described herein as well as immunoassays, employing RIA or ELISA methodologies, based on the production of specific neutralizing antibodies (monoclonal or polyclonal) to natural galectin-1.

Galectin-1 as disclosed herein is said to be "purified" or "substantially free of natural contaminants" if preparations which contain it are substantially free of materials with which this product is normally and naturally found.

As would be apparent to one of ordinary skill in the art, the therapeutic anti-inflammatory effects of galectin-1 may be obtained by providing to a patient the dimeric form of galectin-1 molecules. Further, the therapeutic pro-inflammatory effects of galectin-1 may be obtained by providing the monomeric form of the molecule, or any therapeutically active peptide fragments thereof.

As is also apparent, the therapeutic advantages of galectin-1 may be augmented through the use of galectin-1 mutants or variants possessing additional or substituted amino acid residues added to enhance its coupling to a carrier or to enhance the activity of galectin-1. The scope of the present invention is further intended to include mutant forms of galectin-1 (including galectin-1 molecules which lack certain amino acid residues), or which contain altered amino acid residues, so long as such mutant galectin-1 molecules exhibit the capacity to affect neutrophil activity as described herein for monomeric or dimeric forms of galectin-1 described elsewhere herein.

The galectin-1 polypeptides of the present invention and functional derivatives can be formulated according to known methods of preparing pharmaceutically useful compositions, whereby these materials or their functional derivatives are combined in a mixture with a pharmaceutically acceptable carrier vehicle. Suitable vehicles and their formulation, including other human proteins, e.g., human serum albumin, are described, for example, in *Remington's Pharmaceutical Sciences*, (Mack Publishing Co., 1980).

For reconstitution of a lyophilized product in accordance with this invention, one may employ a sterile diluent, which may contain materials generally recognized for approximating physiological conditions and/or as required by governmental regulation. In this respect, the sterile diluent may contain a buffering agent to obtain a physiologically acceptable pH, such as sodium chloride, saline, phosphate-buffered saline, and/or other substances which are physiologically acceptable and/or safe for use. In general, the material for intravenous injection in humans should conform to regulations established by the Food and Drug Administration, which are available to those in the field.

The pharmaceutical composition may also be in the form of an aqueous solution containing many of the same substances as described above for the reconstitution of a lyophilized product.

The compounds can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

As mentioned above, the products of the invention may be incorporated into pharmaceutical preparations which may be used for therapeutic purposes. However, the term "pharmaceutical preparation" is intended in a broader sense herein to include preparations containing a protein composition in accordance with this invention, used not only for therapeutic purposes but also for reagent or diagnostic purposes as known in the art, or for tissue culture. The pharmaceutical preparation intended for therapeutic use should contain a "pharmaceutically acceptable" or "therapeutically effective amount" of galectin-1 (dimeric or monomeric form), i.e., that amount necessary for preventative or curative health measures. If the pharmaceutical preparation is to be employed as a reagent or diagnostic, then it should contain reagent or diagnostic amounts of galectin-1.

Other Utilities

The present invention also includes methods of detecting galectin-1 or functional derivatives in a sample or subject. For example, antibodies specific for galectin-1 or for functional derivatives thereof, may be detectably labeled with any appropriate ligand, for example, a radioisotope, an enzyme, a fluorescent label, a paramagnetic label, or a free radical. Methods of making and detecting such detectably labeled antibodies or their functional derivatives are well known to those of ordinary skill in the art.

The detection of foci of such labeled antibodies may be indicative of a site of inflammation. In one embodiment, this examination for inflammation is accomplished by removing samples of tissue or blood and incubating such samples in the presence of detectably labeled antibodies. In a preferred embodiment, this technique is accomplished in a non-invasive manner through the use of magnetic imaging, fluorography, etc. For example, such a diagnostic test may be employed to determine a subject's clinical status in rheumatoid arthritis and other chronic inflammatory diseases.

It is possible to use antibodies, or their functional derivatives, to detect or diagnose the presence and location of galectin-1 in a mammalian subject suspected of having an inflammation by utilizing an assay for galectin-1 comprising incubating a biological sample from said subject suspected of containing galectin-1 in the presence of a detectably labeled binding molecule (e.g., antibody) capable of identifying galectin-1 and detecting said binding molecule which is bound in a sample.

Thus, in this aspect of the invention a biological sample may be transferred to nitrocellulose, or other solid support which is capable of immobilizing cells, cell particles or soluble protein. The support may then be washed with suitable buffers followed by treatment with the detectably labeled galectin-1 specific antibody. The solid phase support may then be washed with the buffer a second time to remove unbound antibody. The amount of bound label on the antibody may then be detected by conventional means.

In carrying out the assay of the present invention on a sample containing galectin-1, the process comprises:

(a) contacting a sample suspected of containing galectin-1 with a solid support to effect immobilization of galectin-1;

(b) contacting said solid support with a detectably labeled galectin-1-specific antibody;

(c) incubating said detectably labeled galectin-1-specific antibody with said support for a time sufficient to allow the galectin-1-specific antibody to bind to the immobilized galectin-1;

(d) separating the solid phase support from the incubation mixture obtained in step (c); and (e) detecting the bound label and thereby detecting and quantifying galectin-1.

This aspect of the invention relates to a method for detecting galectin-1 or fragment thereof in a sample, comprising:

(a) contacting the sample suspected of containing galectin-1 with a galectin-1-specific antibody or fragment thereof which binds to galectin-1; and (b) detecting whether a complex is formed.

Of course, the specific concentrations of detectably labeled antibody and galectin-1, the temperature and time of incubation, as well as other assay conditions may be varied, depending on various factors including the concentration of galectin-1 in the sample, the nature of the sample, and the like. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which the galectin-1-specific antibody can be detectably labeled is by linking the same to an enzyme. This enzyme, in turn when later exposed to its substrate, will react with the substrate in such a manner as to produce a chemical moiety which can be detected, for example, by spectrophotometric, fluorometric or by visual means. Enzymes which can be used to detectably label the galectin-1-specific antibody include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase glucoamylase and acetylcholine esterase.

The galectin-1 specific-antibody may also be labeled with a radioactive isotope which can be determined by such means as the use of a gamma counter or a scintillation counter or by audioradiography. Isotopes which are particularly useful for the purpose of the present invention are: $^{3}H$, $^{125}I$, $^{131}I$, $^{35}S$, $^{14}C$, and $^{51}Cr$.

It is also possible to label the galectin-1-specific antibody with a fluorescent compound. When the fluorescently labeled antibody is exposed to light of the proper wave length, its presence can then be detected due to the fluorescence of the dye. Among the most commonly used fluorescent labelling compounds are fluorescein isothiocyanate rhodamine, phycoerytherin, phycocyanin, allophycocyanin, o-phthaldehyde and fluorescamine.

The galectin-1-specific antibody can also be detectably labeled using fluorescence emitting metals such as $^{152}Eu$, or others of the lanthanide series. These metals can be attached to the galectin-1-specific antibody using such metal chelating groups as diethylenetriaminepentaacetic acid (DTPA) or ethylenediaminetetraacetic acid (EDTA).

The galectin-1-specific antibody also can be detectably labeled by coupling it to a chemiluminescent compound. The presence of the chemiluminescent-tagged galectin-1-specific antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the galectin-1-specific antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the galectin-1-specific antibody may be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection may also be accomplished by visual comparison of the extent to enzymatic reaction of a substrate in comparison with similarly prepared standards.

In one embodiment of the invention, galectin-1 can be used to screen for agents that activate neutrophil cells. This assay is based on the ability of activated, but not non-activated, cells to be agglutinated by galectin-1. In one version, cells would be treated in microtiter wells with the new agent and the visual agglutination of the cells by galectin-1 within minutes would demonstrate activation of the neutrophils.

In another embodiment, galectin-1 can be used to screen for compounds that block neuraminidase (sialidase) action. Activated neutrophils express a neuraminidase that exposes binding sites for galectin-1. Inhibitors of the neuraminidase would block agglutination of activated cells by galectin-1.

In another embodiment, immobilized galectin-1 can be used to physically separate activated neutrophils from non-activated cells. Only the activated cells would bind to immobilized lectin. Thus, one could prepare pure populations of either activated or nonactivated cells.

In another embodiment potential new pro-inflammatory drugs or compounds can be screened by their ability to block agglutination of activated neutrophils by dimeric galectin-1. Such inhibitors could be carbohydrate-based, for example, or could be other organic compounds that mimic such a carbohydrate, for example. Alternatively, one of ordinary skill in the art can screen for drugs or compounds that prevent or inhibit dimerization of galectin. These drugs could be screened by their ability to block galectin-1 induced agglutination of activated neutrophils.

More particularly, the present invention contemplates a method of screening for compounds which inhibit activation of neutrophils, comprising the steps of providing a sample of non-activated neutrophils, treating the sample with a test compound, exposing the treated sample to conditions which normally cause activation of non-activated neutrophils, and contacting the exposed and treated sample with galectin-1, and wherein when the neutrophils are observed to be substantially non-agglutinated it is concluded that the test compound inhibits the activated of non-activated neutrophils. Where used herein, the term test compound is meant to include proteins (including antibodies), glycoproteins, lipoproteins, as well as peptides, lipids, carbohydrates, or other small molecules.

The present invention also contemplates a method of screening for compounds which inhibit the galectin-1-receptor-mediated biding activity of activated neutrophils, comprising providing a sample of activated neutrophils, treating the sample with a test compound, and contacting the treated sample with galectin-1, and wherein when the neutrophils are observed to be substantially non-agglutinated after being contacted with the galectin-1 it is concluded that the test compound inhibits the galectin-1-receptor-mediated binding activity of the activated neutrophils.

The present invention also contemplates a method of screening for compounds which cause activation of neutrophils, comprising providing a sample of non-activated neutrophils, treating the sample with a test compound, contacting the treated sample with galectin-1, and wherein when the neutrophils are observed to be substantially agglutinated after being contacted with the galectin-1 it is concluded that the test compound causes activation of neutrophils.

The present invention further contemplates a method of screening for compounds which inhibit the binding of galectin-1 to activated neutrophils, comprising providing a sample of activated neutrophils, treating the sample with a test compound, and contacting the treated sample with galectin-1 and wherein when the neutrophils are observed to be substantially non-agglutinated after being contacted with the galectin-1 it is concluded that the test compound inhibits the binding of galectin-1 to activated neutrophils.

The present invention further contemplates a method of screening for compounds which inhibit the apoptosis-inducing effects of galectin-1 on neutrophils comprising providing a sample of activated neutrophils, treating the sample with a test compound, contacting the treated sample with galectin-1, and examining the neutrophils for evidence of apoptosis and wherein when apoptosis of neutrophils fails to be observed, concluding that the test compound inhibits apoptosis of neutrophils by galectin-1.

The present invention further contemplates a method of screening for compounds which stimulate apoptosis of neutrophils via the galectin-1 receptor, comprising providing a sample of activated neutrophils, contacting the sample with a quantity of the monomeric form of galectin-1, treating the contacted sample with a test compound able to stimulate apoptosis of neutrophils, and examining the treated neutrophils for evidence of apoptosis and concluding that the test compound stimulates apoptosis of neutrophils via the galectin-1 receptor when the effectiveness of the test compound in inducing apoptosis is reduced or inhibited.

The present invention further contemplates a method of screening for compounds which bind to the galectin-1 receptor on neutrophils, comprising providing a sample of activated neutrophils, treating the sample with a test compound, and contacting the treated sample with galectin-1, and wherein when the neutrophils are observed to be substantially non-agglutinated, concluding that the test compound binds to the galectin-1 receptor. In particular, the test compound may be a monoclonal antibody.

The invention further contemplates a method of screening for compounds which inhibit expression or activation of neuraminidase in neutrophils, comprising providing a sample of non-activated neutrophils, treating the sample with a test compound, exposing the treated sample to conditions which normally induce the desialylation of neutrophils, and contacting the exposed and treated sample with galectin-1 and wherein when the neutrophils are observed to be substantially non-agglutinated it is concluded that the test compound inhibits the expression or activation of neuraminidase in the neutrophils in the sample.

All of the assay methods listed herein are well within the ability of one of ordinary skill in the art given the teachings provided herein.

Changes may be made in the formulation and the use of the various compositions described herein or in the steps or the sequence of steps of the methods described herein without departing from the spirit and scope of the invention as defined in the following claims.

What is claimed is:

1. A method of screening for compounds which inhibit activation of neutrophils; comprising:

providing a sample of non-activated neutrophils;

treating the sample with a test compound;

exposing the treated sample to conditions which normally cause activation of non-activated neutrophils; and contacting the exposed and treated sample with galectin-1, and concluding that the test compound inhibits the activation of non-activated neutrophils when agglutination of the neutrophils is not observed.

* * * * *

SEQUENCE LISTING

<160> NUMBER OF SEQ ID NOS: 4

<210> SEQ ID NO 1
<211> LENGTH: 6
<212> TYPE: PRT
<213> ORGANISM: hamster

<400> SEQUENCE: 1

Ala Cys Gly Leu Val Ala
 1               5

<210> SEQ ID NO 2
<211> LENGTH: 6
<212> TYPE: PRT
<213> ORGANISM: hamster

<400> SEQUENCE: 2

Ala Ser Gly Leu Val Ala
 1               5

<210> SEQ ID NO 3
<211> LENGTH: 6
<212> TYPE: PRT
<213> ORGANISM: hamster

<400> SEQUENCE: 3

Ala Cys Gly Leu Asp Ala
 1               5

<210> SEQ ID NO 4
<211> LENGTH: 6
<212> TYPE: PRT
<213> ORGANISM: hamster

<400> SEQUENCE: 4

Ala Ser Gly Gln Asp Ser
 1               5